United States Patent [19]

Rivadeneira et al.

[11] Patent Number: 5,332,824
[45] Date of Patent: Jul. 26, 1994

[54] PROCESS FOR THE PREPARATION OF 2-AMINO-5-METHYL-PYRIDINE

[75] Inventors: Eric Rivadeneira, Leverkusen; Klaus Jelich, Wuppertal, both of Fed. Rep. of Germany

[73] Assignee: Bayer Aktiengesellschaft, Leverkusen, Fed. Rep. of Germany

[21] Appl. No.: 43,648

[22] Filed: Apr. 6, 1993

[30] Foreign Application Priority Data

Apr. 15, 1992 [DE] Fed. Rep. of Germany ....... 4212596
Sep. 25, 1992 [DE] Fed. Rep. of Germany ....... 4232175

[51] Int. Cl.$^5$ ................. C07D 213/73; C07D 213/18; C07D 213/20
[52] U.S. Cl. .................................... 546/304; 546/347
[58] Field of Search ........................................ 546/304

[56] References Cited

U.S. PATENT DOCUMENTS 4,386,209 5/1983 McGill et al. ........................ 546/311
4,405,790 9/1983 McGill et al. ........................ 546/304

OTHER PUBLICATIONS

R. A. Abramovitch et al., "Direct Acylamination of Pyridine 1–Oxides", The Journal of Organic Chemistry, vol. 39, No. 13, Jun. 28, 1974, pp. 1795–1802.

R. A. Abramovitch et al., "Direct Acylamination of 3–Substituted . . . the Substituent", J. Org. Chem., vol. 39, No. 13, pp. 1802–1807, (1974).

K. Wachi et al., "Studies on 1,3–Benzoxazines . . . N–Oxides", Chem. Pharm. Bull., 28(2), pp. 465–472 (1980).

Abstract of EP 62,264, 27–Heterocycles, vol. 98, (1983), pp. 541–542.

R. A. Abramovitch, et al., "Regiospecific Animation . . . Polystyrene", Heterocycles, vol. 26, No. 8, (1987), pp. 2065–2068.

V. Boekelheide et al., "Rearrangements of N–Oxides. A Novel . . . Aldehydes", J. Am. Chem. Soc., vol. 76, Mar. 5, 1954, pp. 1286–1291.

Primary Examiner—Alan L. Rotman

Attorney, Agent, or Firm—Sprung Horn Kramer & Woods

[57] ABSTRACT

The invention relates to a novel process and novel intermediates for the preparation of 2-amino-5-methylpyridine (I)

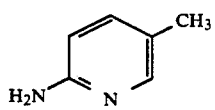

(I)

The process is characterized in that in a first step 3-methyl-pyridine 1-oxide of the formula (II)

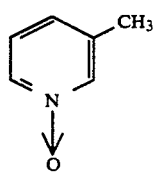

(II)

is reacted with a trialkylamine of the general formula (III)

$R_3N$ (III)

in which
R represents alkyl,
and with an electrophilic compound, in the presence or absence of a diluent, to give the ammonium salt of the general formula (IV)

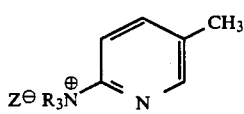

(IV)

in which
R has the abovementioned meaning and
(Arbstract continued on next page.)

$Z^\ominus$ represents an anion formed from an electrophilic compound, the compound (IV)

is, possibly, isolated as a crude intermediate and, possibly, further purified and then in a second step the ammonium salt of the formula (IV) is reacted with hydrogen bromide, in the presence or absence of a diluent, at temperatures between 150° C. and 300° C.

The compound (I) is an intermediate for the preparation of agrochemicals, for example of herbicides.

9 Claims, No Drawings

PROCESS FOR THE PREPARATION OF 2-AMINO-5-METHYL-PYRIDINE

The invention relates to a novel process and novel intermediates for the preparation of 2-amino-5-methyl-pyridine.

It is known that 2-amino-5-methyl-pyridine is obtained when 3-methyl-pyridine is reacted with sodium amide in an inert diluent at elevated temperature and elevated pressure (compare U.S. Pat. No. 4,386,209).

It is further known that 2-amino-5-methyl-pyridine is obtained when 3-methyl-pyridine is reacted with an alkylamine sodium salt in an inert diluent and the 2-alkylamino-5-methyl-pyridine formed in this is dealkylated using hydrogen bromide or hydrogen iodide (compare U.S. Pat. No. 4,405,790).

In both known processes—at least in the initial phase of the reactions—because of the high water-sensitivity of sodium amide or alkylamine sodium salts, strict dryness of all components must be ensured. An additional very large cost factor—in particular because of the safety conditions to be complied with—is represented by the metallic sodium required in each case as starting material.

A novel process has now been found for the preparation of 2-amino-5-methyl-pyridine of the formula (I)

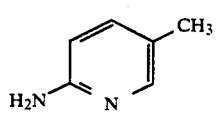

characterised in that in a first step, 3-methyl-pyridine 1-oxide of the formula (II)

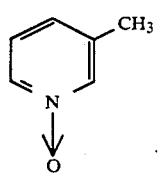

is reacted with a trialkylamine of the general formula (III)

R₃N                (III)

in which
R represents alkyl,
and with an electrophilic compound, in the presence or absence of a diluent, to give the ammonium salt of the general formula (IV)

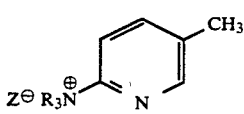

in which
R has the abovementioned meaning and
Z⊖ represents an anion formed from an electrophilic compound, the compound (IV)
is, possibly, isolated as a crude intermediate and, possibly, further purified and then in a second step
a) either the ammonium salt of the formula (IV) is reacted with hydrogen bromide, in the presence or absence of a diluent, at temperatures between 150° C. and 300° C.
b) or alternatively an alkyl compound RZ is cleaved by conventional methods from the compound (IV) and the 2-dialkylamino-5-methyl-pyridine formed during this of the general formula (V)

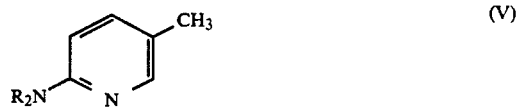

in which
R has the abovementioned meaning,
is reacted with hydrogen bromide, in the presence or absence of a diluent, at temperatures between 150° C. and 300° C.

Surprisingly, 2-amino-5-methyl-pyridine of the formula (I) can be obtained by the process according to the invention in high yield and in considerably improved isomeric purity in comparison to the known processes.

The process according to the invention thus represents a valuable enrichment of the prior art.

The course of the reaction in the process according the invention can for example be outlined by the following formula diagram:

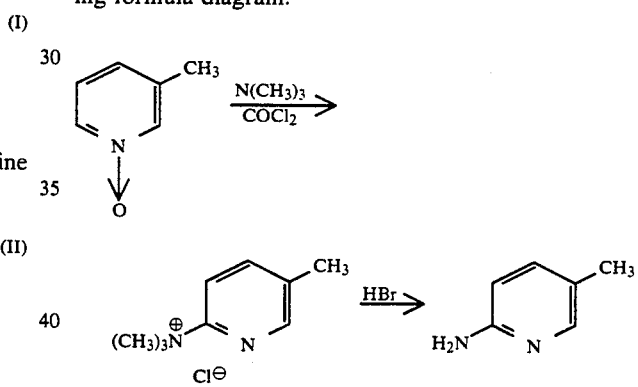

The starting compound of the formula (II) is already known (compare J. Am. Chem. Soc. 76 (1954), 1286–1291).

The trialkylamines to be used as reaction components are generally defined by the formula (III). In the formula (III), NR³ preferably represents $C_1$–$C_4$-alkylamine, in particular trimethylamine or triethylamine.

The ammonium salts formed in the first step of the process according to the invention are generally defined by the formula (IV). In the formula (IV) R preferably represents $C_1$–$C_4$-alkyl, in particular methyl or ethyl; Z⊖ preferably represents a chloride ion or a $C_1$–$C_4$-alkylcarboxylate ion, in particular a chloride ion or an acetate ion.

The 2-dialkyl-amino-5-methyl-pyridines which can be further isolated as intermediates are generally defined by the formula (V). In the formula (V) R preferably represents $C_1$–$C_4$-alkyl, in particular methyl or ethyl.

The 2-dialkylamino-5-methyl-pyridines of the formula (V), in which R represents $C_1$–$C_4$-alkyl, are not yet known in the literature and, as novel chemical compounds, are subject matter of the present patent application. Of the novel compounds of the formula (V), 2- dimethylamino-5-methyl-pyridine and 2-diethylamino-5-methyl-pyridine are particularly preferred.

In the first step of the process according to the invention, an electrophilic compound is used. Preferred electrophilic compounds for the process according to the invention are acid chlorides and acid anhydrides, for example acetyl chloride, propionyl chloride, acetic anhydride, propionic anhydride, benzoyl chloride, benzotrichloride, phosgene, oxalyl chloride, benzenesulphonyl chloride, p-toluenesulphonyl chloride, phosphorus(III) chloride, phosphoryl chloride (phosphorus oxychloride), phosphorus(V) chloride, thionyl chloride, sulphuryl chloride, dichloromethylenedimethylimmonium chloride, cyanuric chloride and chlorotrimethylsilane. Phosgene, thionyl chloride, sulphuryl chloride, benzenesulphonyl chloride and p-toluenesulphonyl chloride are the electrophilic starting substances particularly preferred for the process according to the invention.

The process according to the invention is preferably carried out in the first stage with the use of a diluent. The diluents in question are virtually all inert organic solvents. These include for example aliphatic and aromatic, possibly halogenated, hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl and ethyl acetate, nitriles such as for example acetonitrile and propionitrile, amides such as for example dimethylformamide, dimethylacetamide and N-methyl-pyrrolidone and dimethyl sulphoxide, tetramethylene sulphone and hexamethylphosphoric triamide.

The first step of the process according to the invention, if trimethylamine is used as compound (III), is generally carried out in the temperature range between $-30°$ C. and $+120°$ C., preferably between $-15°$ C. and $+80°$ C. If trialkylamines (III) other than trimethylamine are used, the temperature range of $-30°$ C. to $+15°$ C., preferably between $-15°$ C. and $+10°$ C. is generally employed.

The first step of the process according to the invention is generally carried out at atmospheric pressure. However, it is also possible to employ elevated or reduced pressure, in general between 0.1 and 100 bar.

To carry out the first step of the process according to the invention, for 1 mole of 3-methyl-pyridine 1-oxide of the formula (II), between 1 and 10 mol, preferably between 2 and 5 mol, of trialkylamine of the formula (III) and between 1 and 10 mol, preferably between 2 and 5 mol, of electrophilic compound are generally used.

In a preferred embodiment of the first step of the process according to the invention, the 3-methyl-pyridine 1-oxide of the formula (II) is placed in a diluent and, after cooling, first the trialkylamine and then the electrophilic compound are slowly successively metered in with stirring.

After the reaction is completed, if required, the more readily volatile components are distilled off under reduced pressure. The crude intermediate which essentially contains the ammonium salt of the formula (IV), can be purified in a conventional manner, for example by column chromatography or alternatively used in the crude state in the second step.

The crude intermediate is preferably used as such in the second step.

The second step of the process according to the invention is carried out with or without the use of a diluent. The diluents are, in addition to water, organic solvents, in particular alcohols such as methanol, ethanol or propanol, or carboxylic acids such as acetic acid or propionic acid.

The second step of the process according to the invention is generally carried out in the temperature range between 150° C. and 300° C., preferably between 180° C. and 250° C., In particular between 190° C. and 220° C.

The second step of the process according to the invention is generally carried out at atmospheric pressure. However, it is also possible to employ elevated or reduced pressure, in general between 0.01 and 200 bar.

To carry out the second step of the process according to the invention, the intermediate of the formula (IV) and a solution of hydrogen bromide are preferably mixed at room temperature (approximately 20° C.). The solvent is then distilled off and the reaction mixture is heated to a temperature suitable for the reaction, further hydrogen bromide (solution) being metered in, if required, and, if necessary, solvent being distilled off.

After the reaction is completed, which can be determined by means of thin layer chromatography, the mixture cooled and worked up according to conventional methods.

For example the mixture is shaken with dilute aqueous sodium hydroxide solution and an organic solvent virtually immiscible with water, such as for example ethyl acetate, the organic phase is separated off, dried and filtered. The solvent is carefully distilled off from the filtrate under reduced pressure. A residue remains which essentially contains the product of the formula (I).

Alternatively, in the second process step an alkyl compound RZ can first be cleaved off from the ammonium salts of the formula (IV) by conventional methods with formation of 2-dialkylamino-5-methyl-pyridines of the formula (V). As conventional methods for this can be mentioned for example:

(a) heating with an acid, for example with a hydrogen bromide solution, to a moderately elevated temperature, preferably between 50° C. and 100° C.;

(b) heating with a base, for example with aqueous sodium hydroxide solution, to a moderately elevated temperature, preferably between 50° C. and 150° C. possibly at elevated pressure up to 10 bar;

(c) heating with a solvent, for example with dimethyl sulphoxide to a moderately elevated temperature, preferably between 80° C. and 150° C.

The work-up can be carried out in each case as described above.

The dealkylation of the intermediates of the formula (V) can then carried out analogously to the dealkylation the ammonium salts of the formula (IV) using hydrogen bromide as described above for the preparation of the compound of the formula (I) (compare the preparation examples).

The 2-amino-5-methyl-pyridine which can be prepared by the process according to the invention can be used as an intermediate for the preparation of agrochemicals, for example herbicides (compare EP-A 432600).

PREPARATION EXAMPLES

Example 1 (1st step)

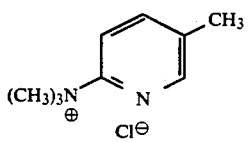

90 g (0.825 mol) of 3-methyl-pyridine 1-oxide are placed in 540 ml of methylene chloride and the mixture is cooled to 0° C. At this temperature, 195 g (3.3 mol) of trimethylamine are condensed in. 245 g (2.63 mol) of phosgene are then passed in, the temperature being maintained an 0° C. by intensive cooling. After completion of the reaction, excess phosgene is eliminated at 20° C. in the vacuum of water jet. The remaining residue is purified by column chromatography (silica gel; eluent: methylene chloride/methanol, 10:1.5 by volume).

188 g of a product mixture are obtained, which, according to the $^1$H-NMR spectrum, contains 102 g (66% of theory) of trimethyl-(5-methyl-pyridin-2-yl)-ammonium chloride.

NMR data: $^1$H-NMR (300 MHz, D$_6$-DMSO) δ/ppm=2.41 (3H, singlet); 3.64 (9H, singlet); 8.06 (2H, AB system, $J_{AB}$=8.4 (1H, singlet).

Example 2 (1st step)

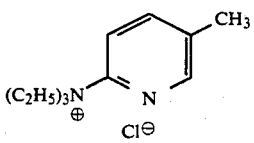

90 g (0.825 mol) of 3-methyl-pyridine 1-oxide are placed in 540 ml of methylene chloride and the mixture is cooled to 0° C. At this temperature, 334 g (3.3 mol) of triethylamine are added. 245 g (2.63 mol) of phosgene are passed in, the temperature being maintained at 0° C. by intensive cooling. After completion of the reaction, excess phosgene is eliminated at 20° C. in the vacuum of a water jet. The remaining residue is purified by column chromatography (silica gel, eluent: methylene chloride/methanol, 10:1.5 by volume).

173 g of a product mixture are obtained, which, according to the $^1$H-NMR spectrum contains 104 g (55% of theory) of triethyl-(5-methyl-pyridin-2-yl)-ammonium chloride.

$^3$H-NMR (300 MHz, CDCl$_3$). δ/ppm=1.20 (9H, triplet, J=7.2 Hz), 2.44 (3H, singlet), 4.14 (6H, quartet, J=7.2 Hz), 7.98 (1H, multiplier, $J_{AB}$=8.4 Hz), 8.34 (1H, quartet, J=0.9 Hz), 8.63 (1H, doublet, $J_{AB}$=8.7 Hz).

Example 3 (1st step)

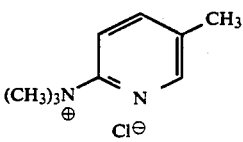

19.5 g (0.331 mol) of trimethylamine are condensed at −10° C. and are added at −5° C. to a solution of 8.8 g (0.0807 mol) of 3-methyl-pyridine 1-oxide in 100 ml methylene chloride. At this temperature, 6.9 ml (0.097 mol) of thionyl chloride are then added dropwise in 10 ml of methylene chloride in the course 30 minutes. The temperature is kept below 0° C. during this process. The resulting yellow solution is left to thaw out and is stirred overnight at room temperature.

A goldish-yellow solution is obtained, which is concentrated at 20°-25° C. on the rotary evaporator. 24.5 g of a greasy solid are produced, which, according to $^1$H-NMR, contains approximately 14.5 g (96% of theory) of trimethyl-(5-methyl-pyridin-2-yl)-ammonium chloride.

$^1$H-NMR: (300 MHz, D$_6$-DMSO) δ/ppm=2.41 (3H, singlet); 3.64 (9H, singlet), 8.06 (2H, AB system, $J_{AB}$=8.4 Hz), 8.5 (1H, singlet).

Example 4 (1st step)

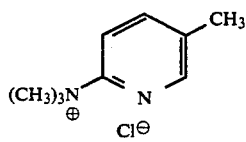

20.5 g (0.348 mol) of trimethylamine are condensed at −10° C. and are then added to a solution of 8.8 g (0.0807 mol) of 3-methyl-pyridine 1-oxide in 110 ml of methylene chloride at −5° C. At this temperature, a solution of 21.3 ml (0.2421 mol) of sulphuryl chloride in 20 ml of methylene chloride is then added dropwise. A white fine precipitate forms. The mixture is allowed to thaw for a period of one hour at room temperature and is then stirred for a further 2 hours at this temperature. The precipitate dissolves completely in this time. The resulting goldish-yellow solution is allowed to stand overnight and is then concentrated on the rotary evaporator.

48.7 g of a greasy solid are obtained, which, according to $^1$H-NMR, contains 11.6 g (77% of theory) of trimethyl(5-methyl-pyridin-2-yl)-ammonium chloride.

Example 5 (2nd step)

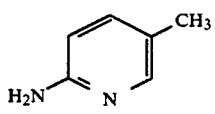

35 ml of a 48% strength hydrogen bromide solution are added to 32 g of a crude mixture produced by reaction of 3-methyl-pyridine 1-oxide with trimethylamine and phosgene, which crude mixture, according to $^1$H-NMR, contains 19.3 g (0.035 mol) of trimethyl-(5-methyl-pyridin-2-yl)ammonium chloride. The water is distilled off and then the mixture is heated to 210° C. At this temperature, 48% strength hydrogen bromide solution is added dropwise and water is distilled off. After 8 hours, the reaction is completed according to thin layer chromatography. The mixture is allowed to cool and is adjusted to pH 9 using dilute sodium hydroxide solution. The mixture is then extracted four times using ethyl acetate. The combined extracts are dried over sodium sulphate and concentrated, following filtration, on the rotary evaporator.

9.3 g (83% of theory) of 2-amino-5-methylpyridine are obtained, which, according to gas chromatographic analysis, contain 1% of 2-amino-3-methylpyridine.

Example 6 (2nd step)

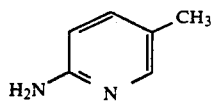

25 g of a crude mixture produced by reaction of 3-methylpyridine 1-oxide with trimethylamine and thionyl chloride which, according to ¹H-NMR, contains 13.06 g (0.07 of trimethyl-(5-methyl-pyridin-2-yl)-ammonium chloride are mixed with 80 ml of a 48% strength hydrogen bromide solution and then heated to 80° C. After 1.5 hours, the mixture is allowed to cool and 25 ml of pyridine are slowly added with ice cooling. Water and pyridine are then distilled off on a descending condenser at an bath temperature of 150° C. The oil bath temperature increased to 210° C. The mixture is stirred for 12 hours at this temperature. The mixture is then allowed to cool and is adjusted to pH 9–10 using dilute sodium hydroxide solution. After extracting three times using ethyl acetate, the combined extracts are dried over sodium sulphate, filtered and concentrated on the rotary evaporator. In the oil pump vacuum the residue of pyridine is removed.

6.5 g (86% of theory) of 2-amino-5-methylpyridine are obtained, which, according to gas chromatographic analysis, contain approximately 1% of 2-amino-3-methylpyridine.

Example 7 (1 st +2nd step)

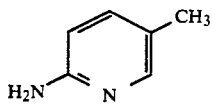

2.2 g (0.377 mol) of trimethylamine are condensed at −10° C. and added at −5° C. to a solution of 10.03 g (0.092 mol) of 3-methyl-pyridine 1-oxide in 120 ml of methylene chloride. At this temperature, 7.9 (0.11 mol) of thionyl chloride in 15 ml of methylene chloride are then added dropwise in the course of 30 minutes. The temperature during this process is kept below 0° C. The resulting yellow solution is allowed to thaw and is stirred overnight at room temperature. The solvent is removed in vacuo. 35 ml of a 48% strength hydrogen bromide solution are then added. The water distilled off and the mixture is then heated to 210° C. 48% strength hydrogen bromide solution is added dropwise continuously and water is distilled off. After 8 hours, the reaction is completed according to thin layer chromatography. The mixture is allowed to cool and is adjusted to pH 9 using dilute sodium hydroxide solution. The mixture is then extracted four times using ethyl acetate. The combined extracts are dried over sodium sulphate and concentrated, after filtration, on the rotary evaporator.

8 g (80.5% of theory) of 2-amino-5-methyl-pyridine are obtained.

INTERMEDIATES OF THE FORMULA (V)

Examples (V-1)

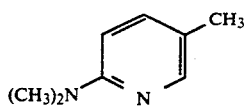

23 g of a crude mixture obtained by reaction of 3-methylpyridine 1-oxide with trimethylamine and thionyl chloride, which crude mixture, according to ¹H-NMR, contains 12.69 g (0.068 mol) of trimethyl-(5-methylpyridin-2-yl)-ammonium chloride, is mixed with 80 ml of a 48% strength hydrogen bromide solution and then heated to 80° C. After 1.5 hours, the mixture is allowed to cool and is adjusted to pH 9 using sodium hydroxide solution. The mixture is extracted three times using ethyl acetate.

After drying the combined organic phases, filtration and elimination of the solvent on the rotary evaporator, 8.8 g (95% of theory) of 2-dimethylamino-5-methyl-pyridine are obtained.

¹H-NMR (300 MHz, CDCl₃):

δ/ppm=2.17 (3H, singlet), 3.04 (6H, singlet), 6.45 (1H, doublet, $J_{AB}$=8.7 Hz), 7.27 (1H, multiplier, $J_{AB}$=8.7 Hz), 7.99 (1H, quartet, J=0.9 Hz)

Example (V-2)

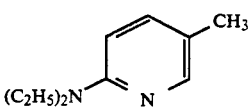

10 g of a crude mixture obtained by reaction of 3-methylpyridine 1-oxide with triethylamine and phosgene and subsequent purification by column chromatography, which crude mixture, according to the ¹H-NMR spectrum, contains 6 g (0.026 mol) of triethyl-(5-methyl-pyridin-2-yl)ammonium chloride, are added to 50 ml of dilute sodium hydroxide solution and stirred for 4 hours at 60° C. After cooling the mixture to room temperature, it is extracted three times using methylene chloride.

After drying the combined extracts over sodium sulphate, filtration and elimination of the solvent on the rotary evaporator, 4.05 g (95% of theory) of 2-diethylamino-5-methylpyridine are obtained.

Example (V-3)

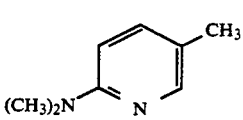

Approximately 10 ml of DMSO are added to 10 g of a crude mixture resulting from the reaction of 3-methylpyridine 1-oxide with trimethylamine and phosgene, which crude mixture, according to ¹H-NMR, contains 4.5 g (0.024 mol) of trimethyl-(5-methyl-pyridin-2-yl)-ammonium chloride, and the mixture is heated to 120° C. with stirring. The mixture is stirred for 2 hours at this temperature. The mixture is then cooled to room temperature and adjusted to pH 1 using hydrochloric acid. After extracting for three times using methylene chloride, the aqueous phase is brought to pH 12 by addition of sodium hydroxide solution. The mixture is again extracted three times using methylene chloride. The extracts of the alkaline phase are combined, dried over sodium sulphate and, after filtration, concentrated on the rotary evaporator.

5.9 g of a crude mixture are obtained, which, according to $^1$H-NMR and GC analysis, contains 3.05 g of 2-dimethylamino-5-methyl-pyridine (93% of theory).

$^1$H-NMR: (300 MHz, CDCl$_3$)

δ/ppm=2.17 (3H, singlet), 3.04 (6H, singlet), 6.45 (1H, doublet, $J_{AB}$ =8.7 Hz), 7.27 (1H, multiplier, $J_{AB}$=8.7 Hz), 7.99 (1H, quartet, J=0.9 Hz).

Example 8

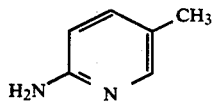

4 g (0. 029 mol) of 2-dimethylamino-5-methyl-pyridine are added with cooling to 44 ml of 48% strength hydrobromic acid. 26 ml of pyridine are added likewise with cooling. The mixture is heated for 5 hours to 150° C. (oil bath temperature). The water present initially is distilled off in this time. The oil bath temperature is then increased to 220° C. and the mixture is stirred for a further 2 hours at this temperature. The batch is then cooled to room temperature and the mixture is then added to water. The mixture is then brought to pH 9 using sodium hydroxide solution. The mixture is extracted three times using methylene chloride, the combined extracts are dried using sodium sulphate and, after filtration, concentrated on the rotary evaporator. The last residues of pyridine are then eliminated in the oil pump vacuum.

3 g (95% of theory) of 2-amino-5-methylpyridine are obtained.

We claim:

1. A process for the preparation of 2-amino-5-methyl-pyridine of the formula

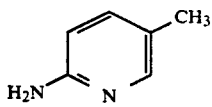 (I)

which comprises in a first step reacting 3-methyl-pyridine 1-oxide of the formula

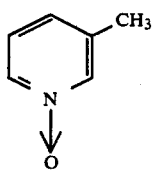 (II)

with a trialkylamine of the formula (R)$_3$N     (III)

in which

R is C$_1$-C$_4$-alkyl, and with an electrophilic compound selected from the group consisting of acetyl chloride, propionyl chloride, acetic anhydride, propionyl anhydride, benzoyl chloride, benzotrichloride, phosgene, oxalyl chloride, benzene sulfonyl chloride, p-toluene sulfonyl chloride, phosphorous (111)chloride, phosphorous oxy chloride, phosphorous (V) chloride, thionyl chloride, sulfonyl chloride dichloromethylene-dimethyl-immonium chloride, cyanuric chloride and chlorotrimethyl-silane, in the presence or absence of a diluent, to given the ammonium salt of the formula

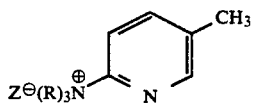 (IV)

in which

Z is an anion from the electrophilic compound, optionally isolating the compound (IV), optionally purifying the compound (IV), optionally cleaving the compound (IV) into an alkyl compound RZ and a 2-dialkylamino-5-methyl-pyridine of the formula

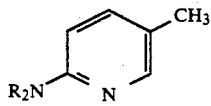 (V)

and then in a second step reacting the compound (IV) or (V) with hydrogen bromide at a temperature between 150° and 300° C.

2. A process according to claim 1 wherein Z$^-$ is a chloride ion or C$_1$-C$_4$-alkylcarboxylate ion.

3. A process according to claim 1, wherein

R is methyl or ethyl, and

Z$^-$ is a chloride ion or acetate ion.

4. A process according to claim 1, wherein the first step is carried out in the presence of an inert organic solvent as diluent.

5. A process according to claim 1, wherein R is methyl and the first reaction step is carried out in the temperature range between −30° C. and +120° C.

6. A process according to claim 1, wherein (R)$_3$N is other than trimethylamine and the first reaction step is carried out in the temperature range between −30° C. and +15° C.

7. A process according to claim 1, wherein per mol of 3-methyl-pyridine-1-oxide (II), there are used between 1 and 10 mols of trialkylamine (III) and between 1 and 10 mols of the electrophilic compound.

8. A process according to claim 1, wherein in the second step compound (IV) is reacted in the presence of a diluent selected from the group consisting of water and an organic solvent at a temperature between 180° and 250° C.

9. A process according to claim 1, wherein before the second step compound (IV) is cleaved by a) heating with an acid or b) heating with a base or c) heating with a solvent.

* * * * *